(12) United States Patent
Roy et al.

(10) Patent No.: US 9,096,830 B2
(45) Date of Patent: Aug. 4, 2015

(54) MULTI-LAYERED HYDROGEL CONSTRUCTS AND ASSOCIATED METHODS

(75) Inventors: Krishnendu Roy, Austin, TX (US); Lonnissa Nguyen, Cambridge, MA (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 778 days.

(21) Appl. No.: 13/093,606

(22) Filed: Apr. 25, 2011

(65) Prior Publication Data
US 2011/0262493 A1 Oct. 27, 2011

Related U.S. Application Data

(60) Provisional application No. 61/327,168, filed on Apr. 23, 2010.

(51) Int. Cl.
| | | |
|---|---|---|
| A01N 63/00 | (2006.01) | |
| C12N 5/077 | (2010.01) | |
| A61L 27/22 | (2006.01) | |
| A61L 27/38 | (2006.01) | |
| A61L 27/52 | (2006.01) | |

(52) U.S. Cl.
CPC ............. *C12N 5/0655* (2013.01); *A61L 27/227* (2013.01); *A61L 27/3839* (2013.01); *A61L 27/52* (2013.01); *A61L 2430/06* (2013.01); *C12N 2513/00* (2013.01); *C12N 2533/30* (2013.01); *C12N 2533/70* (2013.01); *C12N 2533/80* (2013.01)

(58) Field of Classification Search
CPC ...................... A61B 17/12145; A61L 27/227
USPC ........................................... 435/287.1, 287.8
See application file for complete search history.

(56) References Cited

PUBLICATIONS

Kim et al. "Bone regeneration using hyaluronic acid-based hydrogel with bone morphogenic protein-2 and human mesenchymal stem cells", Biomaterials, 2007, 28:1830-1837.*
Fan et al. "Cartilage regeneration using mesenchymal stem cells and a PLGA-geltin/chondroitin/hyaluronate hybrid scaffold" Biomaterials, 2006, 27:4573-4580.*
He, et al. "Material properties and cytocompatibility of injectable MMP degradable poly(lactide ethylene oxide fumarate) hydrogel as a carrier for marrow stromal cells", Biomacromolecules, 2007, 8:780-792.*
Burdick, J.A and K.S. Anseth. Photoencapsulation of osteoblasts in injectable RGD-modified PEG hydrogels for bone tissue engineering. Biornaterials, 2002. 23(2): p. 4315-23.
Bryant, S.J., et al., Encapsulating chondrocytes in degrading PEG hydrogels with high modulus: engineering gel structural changes to facilitate cartilaginous tissue production. Biotechnol Bioeng, 2004. 86(7): p. 747-55.
Bryant, S.J., et al., Crosslinking density influences the morphology of chondrocytes photoencapsulated in PEG hydrogels during the application of compressive strain, J Orthop Res, 2004. 22(5): p. 1143-9.
Bryant, S.J. and K.S. Anseth, Controlling the spatial distribution of ECM components in degradable PEG hydrogels for tissue engineering cartilage. J Biomed Mater Res A, 2003. 64(1): p. 70-9.
Alcantar, N.A., E.S. Aydil, and J.N. Israelachvili, Polyethylene glycol-coated biocompatible surfaces. J Biomed Mater Res, 2000. 51(3): p. 343-51.
Klein, T.J., et al., Tissue Engineering of Articular Cartilage with Biomimetic Zones. Tissue Eng Part B Rev, 2009.
Sharma, B., et al., Designing zonal organization into tissue-engineered cartilage. Tissue Eng, 2007. 13(2): p. 405-14.
Ng, K.W., G.A. Ateshian, and C.T. Hung, Zonal chondrocytes seeded in a layered agarose hydrogel create engineered cartilage with depth-dependent cellular and mechanical inhomogeneity. Tissue Eng Part A, 2009. 15(9): p. 2315-24.
Schinagl, R.M., et al., Depth-dependent confined compression modulus of full thickness bovine articular cartilage. J Orthop Res, 1997. 15(4): p. 499-506.
Bhosale, A.M. and J.B. Richardson, Articular cartilage: structure, injuries and review of management. Br Med Bull, 2008. 87: p. 77-95.
Poole, A.R., et al., Composition and structure of articular cartilage: a template for tissue repair. Clin Orthop Relat Res, 2001(391 Suppl): p. 526-33.
Einhorn, T.A., R.J. O'Keefe, and J.A. Buckwaiter, Orthopaedic Basic Science Foundations of Clinical Practice. 3 ed. 2007: American Academy of Orthopaedic Surgeons.
Chen, G., Ushida, Takashi, Tateishi,Tetsuya, Scaffold Design for Tissue Engineering. Macromolecular Bioscience, 2002. 2: p. 67-77.
Varghese, S., et al., Chondroitin sulfate based niches for chondrogenic differentiation of mesenchymal stem cells. Matrix Biol, 2008. 27(1): p. 12-21.
Butnariu-Ephrat. M., et al., Resurfacing of goat articular cartilage by chondrocytes derived from bone marrow. Clin Orthop Relat Res, 1996(330): p. 234-43.
Nuttelman, C.R., M.C. Tripodi, and K.S. Anseth, In vitro osteogenic differentiation of human mesenchymal stem cells photoencapsulated in PEG hydrogels. J Biomed Mater Res A, 2004. 68(4): p. 773-62.
Kim, S., et al., Synthetic MMP-13 degradable ECMs based on poly(N-isopropylacrylamide-co-acrylic acid) semi-interpenetrating polymer networks. I. Degradation and cell migration. J Biomed Mater Res A, 2005. 75(1): p. 73-88.

(Continued)

*Primary Examiner* — Bin Shen
(74) *Attorney, Agent, or Firm* — Baker Botts L.L.P.

(57) ABSTRACT

Multi-layered hydrogel constructs comprising: a first layer comprising a first polymerizable material, hyaluronic acid and a plurality of cells; a second layer comprising a second polymerizable material, chondroitin sulfate and a plurality of cells; and a third layer comprising a third polymerizable material, chondroitin sulfate, a matrix metalloprotease sensitive peptide, and a plurality of cells are provided. Associated methods are also provided.

9 Claims, 7 Drawing Sheets
(6 of 7 Drawing Sheet(s) Filed in Color)

(56) References Cited

PUBLICATIONS

Kim, S. and K.E. Healy, Synthesis and characterization of injectable poly(N-isopropylacrylamide-co-acrylic acid) hydrogels with proteolytically degradable cross-links. Biomacromolecules, 2003. 4(5): p. 1214-23.

Seliktar, D., et al., MMP-2 sensitive, VEGF-bearing bioactive hydrogels for promotion of vascular healing. J Biomed Mater Res A, 2004. 68(4): p. 704-16.

Bryant, S.J. and K.S. Anseth, Hydrogel properties influence ECM production by chondrocytes photoencapsulated in poly(ethylene glycol) hydrogels J Biomed Mater Res, 2002 59(1): p. 63-72.

Barry, F., et al., Chondrogenic differentiation of mesenchymal stem cells from bone marrow: differentiation-dependent gene expression of matrix components. Exp Cell Res, 2001. 268(2): p. 189-200.

Williams, C.G., et al., In vitro chondrogenesis of bone marrow-derived mesenchymal stem cells in a photopolymerizing hydrogel. Tissue Eng, 2003.9(4): p, 679-68.

Eyre, D.R. and J.J. Wu, Collagen of fibrocartilage: a distinctive molecular phenotype in bovine meniscus. FEBS Lett, 1983. 158(2): p. 265-70.

Harper, J. and M. Klagsbrun, Cartilage to bone—angiogenesis leads the way. Nat Med, 1999.5(6): 617-8.

He, X. and E. Jabberi, Material properties and cytocompatibility of injectable MMP degradable poly(lactide ethylene oxide fumarate) hydrogel as a carrier for marrow stromal cells, Biomacromolecules, 2007. 8(3): p. 780-92.

Leach, B.J., Bivens, K. A. Patrick, C. W., Jr., Schmidt, C. E., Photocrosslinked hyaluronic acid hydrogels: natural, biodegradable tissue engineering scaffolds. Biotechnol Bioeng, 2003. 82(5): p. 578-89.

* cited by examiner

Compressive Modulus of Hydrogel Constructs

| Hydrogel Groups | Blanks | | 2 Weeks | | 4 Weeks | | 6 Weeks | |
|---|---|---|---|---|---|---|---|---|
| | Compressive Modulus (kPa) | Standard Error | Compressive Modulus (kPa) | Standard Error | Compressive Modulus (kPa) | Standard Error | Compressive Modulus (kPa) | Standard Error |
| PEG | 293.21 | ± 39.18 | 197.65 | ± 25.51 | 512.59 | ± 96.62 | 751.18 | ± 54.86 |
| PEG:MMP | 261.88 | ± 1.51 | 244.41 | ± 37.00 | 492.34 | ± 40.47 | 603.99 | ± 64.26 |
| CS | 82.39 | ± 38.82 | 26.42 | ± 5.80 | 65.03 | ± 9.98 | 68.18 | ± 37.37 |
| PEG:CS | 117.8 | ± 54.46 | 121.14 | ± 36.00 | 284.00 | ± 89.96 | 270.87 | ± 31.55 |
| PEG:CS:MMP | 105.78 | ± 26.89 | 120.33 | ± 28.62 | 147.88 | ± 21.01 | 209.1 | ± 38.16 |
| HA | 31.48 | ± 8.86 | 41.66 | ± 14.12 | 11.60 | ± 4.68 | | |
| PEG:HA | 330.6 | ± 19.13 | 271.57 | ± 64.21 | 435.07 | ± 59.52 | 1227.93 | ± 102.14 |
| PEG:HA:MMP | 184.28 | ± 26.76 | 201.41 | ± 4.77 | 360.63 | ± 54.56 | 666.73 | ± 118.35 |
| PEG:CS:HA | 74.02 | ± 11.10 | 92.19 | ± 10.47 | 204.50 | ± 77.75 | 521.79 | ± 31.39 |
| PEG:CS:HA:MMP | 67.86 | ± 2.55 | 80.30 | ± 13.46 | 159.96 | ± 17.85 | 389.44 | ± 59.70 |

US 9,096,830 B2

MULTI-LAYERED HYDROGEL CONSTRUCTS AND ASSOCIATED METHODS

CROSS-REFERENCE TO RELATED APPLICATIONS

The application claims the benefit of U.S. Provisional Application Ser. No. 61/327,168, filed Apr. 23, 2010, the entire disclosure of which is hereby incorporated by reference.

BACKGROUND

Cartilage regeneration is one of the most widely studied areas in tissue-engineering. Biomaterial-based scaffolds, especially polyethylene glycol (PEG)-based hydrogels, have been established as a conductive environment for chondrogenic differentiation of progenitor cells. However, despite significant progress, one of the major unsolved challenges has been regenerating tissue that mimics the highly organized zonal architecture of articular cartilage, from superficial to middle and deep zones as well as the calcified zone in the osetochondral junction. Few recent studies have attempted to create such spatial organization, but only using zone-specific chondrocytes isolated from native cartilage. Efforts to generate zonally-organized cartilage-like tissue starting from stem or progenitor cell populations are yet to be reported.

Figure 1A:
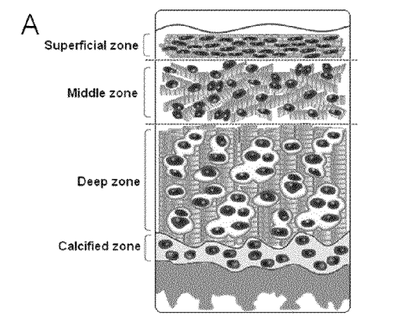
FIG. 1A is schematic illustration of articular cartilage organization depicting the four distinctive zones which include the superficial zone, the middle zone, the deep zone, and the calcified zone.

Anatomically, articular cartilage consists of four, spatially-distinct zones; the superficial, middle, deep, and calcified layers, characterized by unique extra-cellular matrix (ECM) compositions, mechanical properties and cellular organization. (FIG. 1A) The ECM is primarily composed of type II collagen and proteoglycans whose relative concentrations vary spatially from the superficial to the deep layer leading to varying mechanical properties of each zone. The superficial zone contains high levels of collagen II, with thin fibrils and elongated chondrocytes, both arranged parallel to the surface. The proteoglycan content is lowest in this zone. The transitional zone contains randomly oriented collagen II fibers with larger diameters than the superficial zone. The chondrocytes are more rounded and the proteoglycan concentration increases in this zone. The deep zone contains the highest concentration of proteoglycans and the collagen fibers have the largest diameter. The collagen fibers and spherical chondrocytes are arranged in vertical columns perpendicular to the subchondral plate. Finally, the calcified cartilage zone contains high levels of collagen X and integrates the cartilage to the subchondral bone.

SUMMARY

The present disclosure generally relates to tissue engineering. More particularly, the present disclosure relates to multi-layered hydrogel constructs and associated methods.

In one embodiment, the present disclosure provides a multi-layered hydrogel construct comprising: a first layer comprising a first polymerizable material, hyaluronic acid and a plurality of cells; a second layer comprising a second polymerizable material, chondroitin sulfate and a plurality of cells; and a third layer comprising a third polymerizable material, chondroitin sulfate, a matrix metalloprotease sensitive peptide, and a plurality of cells.

In another embodiment, the present disclosure provides a method comprising: providing a first composition comprising a first polymerizable material, hyaluronic acid, and a plurality of cells; crosslinking the first composition until it forms an at least partially gelled first layer; providing a second composition comprising a second polymerizable material, chondroitin sulfate and a plurality of cells; placing the second composition on top of the first layer and crosslinking the second composition until it forms an at least partially gelled second layer; providing a third composition comprising a third polymerizable material, chondroitin sulfate, a matrix metalloprotease sensitive peptide, and a plurality of cells; and placing the third composition on top of the second layer and crosslinking the third composition until it forms an at least partially gelled third layer.

The features and advantages of the present invention will be apparent to those skilled in the art. While numerous changes may be made by those skilled in the art, such changes are within the spirit of the invention.

DRAWINGS

The patent or application file contains at least one drawing executed in color. Copies of this patent or patent application publication with color drawing(s) will be provided by the Office upon request and payment of the necessary fee.

Some specific example embodiments of the disclosure may be understood by referring, in part, to the following description and the accompanying drawings.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to tissue engineering. More particularly, the present disclosure relates to multi-layered hydrogel constructs and associated methods.

Hydrogel constructs of the present disclosure are multi-layer structures with distinctive layers that generally correspond to a particular layer of native articular cartilage. More particularly, each layer comprises certain biomaterials that allow stem cells present within each layer to differentiate into chondrocytes and produce proteins that generally correspond to a particular layer of native articular cartilage. In some embodiments, a multi-layer hydrogel construct of the present disclosure may act as a temporary supportive structure for implantation which will degrade when the chondrocytes have made their own extracellular matrix and integrate themselves with the native tissue. Accordingly, in one embodiment, the present disclosure provides a multi-layered hydrogel construct comprising a first layer comprising a first polymerizable material, hyaluronic acid and a plurality of stem cells; a second layer comprising a second polymerizable material, chondroitin sulfate and a plurality of stem cells; and a third layer comprising a third polymerizable material, chondroitin sulfate, a matrix metalloprotease sensitive peptide, and a plurality of stem cells. Additional layers may also be present.

One of the many advantages of the present disclosure, many of which are not disclosed herein, is that a multi-layered hydrogel construct of the present disclosure utilizes stem cells thereby eliminating the need for donor tissue. Similarly, the present disclosure allows for the simultaneous differentiation a single stem cell population into zone specific chondrocytes. While multi-layer constructs have been utilized before, previous approaches have relied on the use of isolated chondrocytes from a donor and organizing them into layers to create a composite tissue, which can cause additional injury at the isolate site.

In some embodiments, each layer of a multi-layer hydrogel construct of the present disclosure comprises a polymerizable material. Polymerizable material suitable for use in the present disclosure include any suitable polymerizable polymer, monomer, or mixture of monomers and polymers that forms a covalently crosslinked network, with or without the presence of a polymerization initiator, an ionically crosslinked network, or blends of covalently and ionically crosslinked networks. Examples of suitable polymerizable materials may include, but are not limited to, photopolymerizable poly(ethylene glycol) diacrylate (PEGDA) and poly(ethylene glycol). Furthermore, while it is generally desirable for a multi-layered hydrogel construct of the present disclosure to have the same polymerizable material in each layer, it is also possible that a hydrogel construct of the present disclosure may comprise different polymerizable materials for one or more of the layers.

In certain embodiments, a hydrogel construct of the present disclosure may further comprise a polymerization initiator, such as a photoinitiator. A polymerization initiator suitable for use in the present disclosure may comprise any substance that initiates crosslinking of a polymerizable material to form a hydrogel, and includes redox agents, divalent cations such as calcium, and substances that form active species when exposed to visible light and/or UV radiation. A photoinitiator is a specific type of polymerization initiator that generates an active species when exposed to UV light and/or visible light, and can be used to initiate polymerization (i.e., crosslinking) of a photopolymerizable material. Photoinitiators that generate an active species on exposure to UV light are well known to those of skill in the art. In one embodiment, a suitable photoinitiator may comprise Igracure 2959, which is commercially available from Ciba Specialty Chemicals Corp., Tarrytown, N.Y.

In addition to a polymerizable material, each layer of a multi-layer hydrogel construct of the present disclosure comprises a plurality of stem cells. Examples of suitable stem cells include, but are not limited to, marrow stromal cells (MSC) (also known as mesenchymal stem cells) capable of differentiating into chondrocytes, as well as adipose derived stem cells, cord blood cells, induced pluripotent stem cells, embryonic stem cells, etc.

In addition to a polymerizable material and a plurality of stem cells, a first layer of a hydrogel construct of the present disclosure comprises hyaluronic acid. As used herein, the term "hyaluronic acid" includes not only hyaluronic acid, but derivates of hyaluronic acid including, but not limited to, methacrylated hyaluronic acid. In one embodiment, hyaluronic acid may be present in the first layer in an amount of about 0.5 to about 3% (w/v). In one embodiment, a stem cell present within the first layer of a hydrogel construct may differentiate into a chondrocyte and produce proteins that generally correspond to the deep layer of native articular cartilage. More specifically, in one embodiment, a first layer may comprise the highest glycosaminoglycan (GAG) content and a lower collagen II content relative to the other layers within the hydrogel construct.

In addition to a polymerizable material and a plurality of stem cells, a second layer of a hydrogel construct of the present disclosure comprises chondroitin sulfate. As used herein, the term "chondroitin sulfate" includes not only chondroitin sulfate, but derivates of chondroitin sulfate including, but not limited to, methacrylated chondroitin sulfate. In one embodiment, chondroitin sulfate may be present in the second layer in an amount of about 5% to about 20% (w/v). In one embodiment, a stem cell present within the second layer of a hydrogel construct may differentiate into a chondrocyte and produce proteins that generally correspond to the middle layer of native articular cartilage. More specifically, in one embodiment, a second layer may comprise a mid-level glycosaminoglycan (GAG) and collagen II content relative to the other layers within the hydrogel construct.

In addition to a polymerizable material and a plurality of stem cells, a third layer of a hydrogel construct of the present disclosure comprises chondroitin sulfate and a matrix metalloprotease (MMP)-sensitive or MMP-cleavable peptide. In one embodiment, an example of a suitable MMP-sensitive peptide includes a MMP-sensitive peptide represented by the following Formulas I and/or II:

embodiments, it may be desirable to include a layer representative of a calcified cartilage layer. Accordingly, additional layers suitable for use in the hydrogels of the present disclosure may contain pure chondroitin sulfate or another material.

In some embodiments, a hydrogel construct of the present disclosure may further comprise other various additives including, but not limited to, growth factors (e.g., heparin binding growth factor (HBGF), transforming growth factor (TGFα or TGFβ), basic fibroblastic growth factor (bFGF), epidermal growth factor (EGF), vascular endothelium growth factor (VEGF), various angiogenic factors, nerve growth factor (NGF) and muscle morphologic growth factor, cell differentiation factors, other cellular mediators, nutrients, antibiotics, antiinflammatories, and other pharmaceuticals.

The present disclosure also provides method of making a multi-layer hydrogel construct. In one embodiment, a first composition comprising a first polymerizable material, Formula I Formula II In one embodiment, chondroitin sulfate may be present in the third layer in an amount of about 5% to about 20% (w/v) and MMP-sensitive peptide may be present in an amount of about 1 to about 10% (w/v). In one embodiment, a stem cell present within the third layer of a hydrogel construct may differentiate into a chondrocyte and produce proteins that generally correspond to the superficial layer of native articular cartilage. More specifically, in one embodiment, a third layer may comprise a lower glycosaminoglycan (GAG) content and the highest collagen II content relative to the other layers within the hydrogel construct.

In some embodiments, a hydrogel construct of the present disclosure may further comprise additional layers. In such hyaluronic acid and a plurality of cells is prepared and crosslinked until a first layer is formed. Next, a second composition comprising a second polymerizable material, chondroitin sulfate and a plurality of cells is prepared and placed on top of the first layer. This second composition is then crosslinked until a second layer is formed. Finally, a third composition comprising a third polymerizable material, chondroitin sulfate, a matrix metalloprotease sensitive peptide, and a plurality of cells is prepared and placed on top of the second layer. The third composition is then crosslinked until a third layer is formed.

In certain embodiments, crosslinking a composition may comprise providing a polymerization initiator to initiate crosslinking or allowing the composition to polymerize on its own. In one embodiment, a composition may be exposed to an external radiation source, such as a UV lamp, to initiate crosslinking. Furthermore, in some embodiments, the radiation exposure time may be from about 2 to 5 minutes depending upon the degree of gelling desired. Once a hydrogel construct comprising three distinct layers has been formed, the hydrogel may further be subjected to additional crosslinking if desired.

To facilitate a better understanding of the present invention, the following examples of certain aspects of some embodiments are given. In no way should the following examples be read to limit, or define, the entire scope of the invention.

EXAMPLES

Materials and Methods

Hydrogel Fabrication & Characterization

Ten groups of hydrogel scaffolds were fabricated using poly(ethylene glycol) dimethacrylate (PEGDA), MMP-sensitive peptide, and the modified biopolymers. The hydrogels were fabricated by dissolving the materials of each group in phosphate buffered saline (PBS, pH 7.4) containing 0.05 wt % photoinitiator, Irgacure 2959 (2-hydroxy-1-[4-(2-hydroxyethoxy)phenyl]-2-methyl-1-propanone, Ciba Geigy Corp.) and polymerized using a long-wave ultraviolet lamp (Model B100AP, Blak-Ray) at the intensity of ~10 mW/cm$^2$ for 10 minutes. The ten groups of hydrogels are listed in FIG. 1B. Based on previous studies, 20% (w/v) hydrogels were fabricated for the desired compressive strength and HA was incorporated at 1%, CS at equal volume and MMP-sensitive peptide at equimolar ratio with PEG. The degradation profiles of each hydrogel composition were determined by swelling the hydrogels in PBS overnight, and then degraded in 1.5 mL of collagenase (25 µg/mL), hyaluronidase (500 U/mL) or chondroitinase (0.15 U/mL) which was replaced every 72 hours. The hydrogels were incubated at 37° C. on an orbital shaker and at various times points the hydrogels were removed to obtain their swollen weight (n=3). The percent weight remaining of each hydrogel was recorded over time based on the initial swollen weight. The swelling properties were determined by swelling the hydrogels after polymerization in PBS for 72 hours to reach equilibrium. The hydrogels were then lyophilized over night to obtain their dry weight. The changes in hydrogel weight between drying and swelling were used to determine the volumetric swelling ratio and equilibrium water content. The compressive modulus of the hydrogels were determined at room temperature on an Inspec 2200 Instron with a 125 N loading cell (0.1 mm/sec).

Multi-Layer Hydrogel Fabrication

Figure 4A:
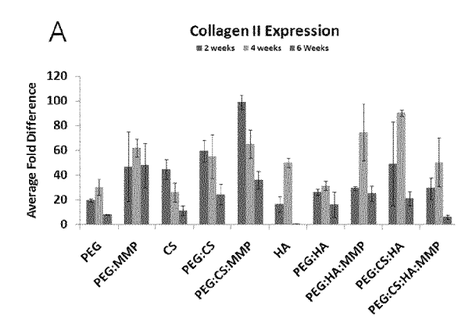
FIG. 4A is graph illustrating the average fold difference for collagen II for each hydrogel construct.

To fabricate a multi-layered hydrogel, the first layer was prepared by polymerizing 100 µL of a PEG:HA-marrow stromal cell (MSC) mixture under UV for 3 minutes to represent the deep zone. Next, 100 µL of a PEG:CS-MSC mixture was added on top of the partially polymerized first layer and it was polymerized under UV for an additional 3 minutes to represent the transitional zone. Finally, for the superficial zone, 100 µL of PEG:CS:MMP was added and the entire hydrogel was polymerized for 5 minutes. A schematic illustration of a layered hydrogel according to one embodiment is shown in FIG. 4A. This multi-layered composition was cultured in serum free chondrogenic media.

Fabrication and Culture of MSC in Various Hydrogel Constructs

Figure 1B:
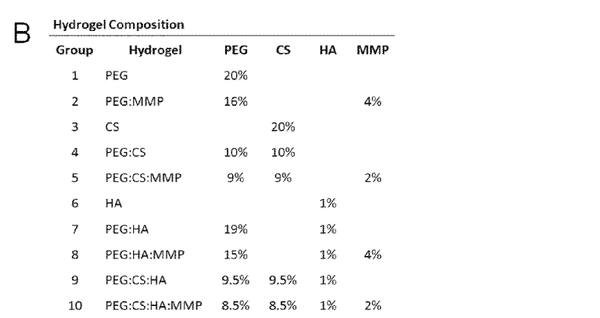
FIG. 1B is a table indicating ten groups of hydrogels and their various material compositions. All hydrogels are fabricated at 20% (w/v) to ensure sufficient mechanical strength is achieved with the exception of pure chondroitin sulfate and hyaluronic acid hydrogels.

D1 bone marrow progenitor cells were encapsulated within the single and multi-layered hydrogel constructs listed in FIG. 1B. 20 million cells/mL were mixed with the syringe filtered polymer solution. Then, 100 µL of the cell/polymer mixture was polymerized for 10 minutes using a long-wave ultraviolet lamp (Model B100AP, Blak-Ray) at the intensity of ~10 mW/cm$^2$. The hydrogels were cultured in serum free chondrogenic media containing 1% penicillin/streptomycin, 10 nM Dexamethasone, 50 µg/mL ascorbic acid-2-phosphate, 40 µg/mL L-proline, 5 mL ITS+1, and 10 ng/mL TGF-$\beta$1 for 2, 4 and 6 weeks in a 12-well plate. The media was changed every other day.

RNA Isolation and RT-PCR Analyses

The hydrogels were removed from culture and the gene expressions of encapsulated cells were analyzed. The hydrogels were placed in 2 mL tubes and 200µ of Trizol® was added to the tubes. The hydrogels were then crushed using a homogenizer (Wheaton). After homogenization, 800 µL of Trizol® was added to the tube. The RNA isolation was performed following the manufacture's protocol. Genomic DNA was removed using Deoxyribonuclease I (Invitrogen). The first strand of cDNA was synthesized by reverse transcription (RT) using Superscript™ III kit (Invitrogen), following the manufacturer's instructions.

Immunohistochemistry Staining for Collagen II and X

Histology of the hydrogel constructs was performed to investigate the chondrogenic differentiation and verify the quantitative real time data. At 2, 4, and 6 week time points, hydrogels were removed from culture and fixed in 4% paraformaldehyde at 4° C. for an overnight period. Fixed hydrogels were then dehydrated for paraffin embedding using 1-hr sequential steps in increasing ethanol solution. Paraffin-embedded hydrogels were sliced in transverse sections at 10 µm using a rotary microtome. Immunohistochemistry was performed to stain collagen II (green) and collagen X (red). Rabbit polyclonal antibodies to collagen II and collagen X (AbCam) were used as primary antibodies to fluorescently label the sectioned hydrogels. The slides were imaged using a confocal fluorescence microscope (Leica SP2 AOBS).

Biochemical Characterization

Glycosaminoglycan (GAG) production was determined using the Dimethylmethylene blue (DMMB) assay. Briefly, at 2, 4, and 6 week time points, hydrogels were removed from culture. Wet weights (ww) and dry weights (dw) after 48 hours of lyophilization were obtained for each construct (n=3). The dry constructs were then digested in 1 mL of papainase (papain, 125 µg/mL; Sigma) at 60° C. overnight. 200 µL of the DMMB solution was added to each well of the 96 well plates and then 50 µL of standard and samples were added. The fluorescence was read at 525 nm. To account for the hydrogel material, absorbance of blank hydrogels were subtracted from the sample values. The DNA content was determined using Sigma's DNA quantification kit (DNA-QF) in order to normalize the GAG production. The assay was carried out following the manufacture's protocol for multi-wall assay. The fluorescence was read at 360 excitation and 460 emissions.

Statistical Analysis

All quantitative data were expressed as mean±standard deviation and were verified by analysis of variance using one way ANOVA with the Fisher correction. P values of less than 0.05 were considered statistically significant.

Results

Ten groups of hydrogels using various concentrations of PEG, MMP-sensitive peptide, CS, and HA (FIG. 1B) were fabricated as detailed above. After fabricating these materials, the physical properties of each hydrogel were then characterized to determine if they had similar characteristics to that of native cartilage.

Figure 1C:
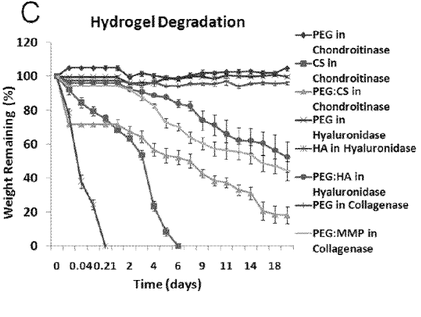
FIG. 1C is a graph illustrating the degradation profiles of PEG-based hydrogels incorporating chondroitin sulfate (CS), hyaluronic acid (HA) and matrix metalloprotease (MMP) sensitive peptide. The percent mass loss of hydrogel was recorded over time based on the initial swollen weight and the weight at each time point.

FIG. 1C shows the degradation profiles for the hydrogels. As expected, the PEG hydrogels did not degrade in any of the enzyme solutions while pure CS and HA hydrogels degraded very rapidly. Incorporating CS, HA, and MMP-sensitive peptide into the PEG hydrogels made them degradable. Incorporating CS into the hydrogels demonstrated the fastest degradation kinetics while incorporating HA resulted in the slowest degradation rates.

Figure 1D:
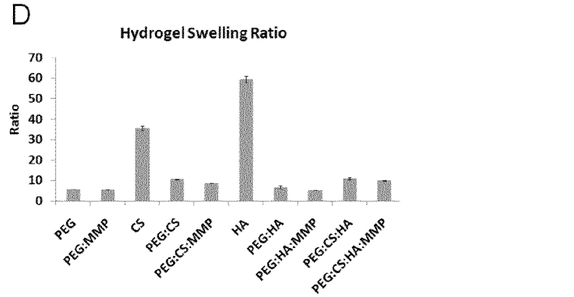
FIG. 1D is a graph illustrating the volumetric swelling ratios, which correlate to the ability of the hydrogels to absorb water.

The volumetric swelling ratios shown in FIG. 1D reveal that the hydrogels containing the MMP-sensitive peptide exhibited a lower swelling ratio than their corresponding constructs without the MMP-sensitive peptide. However the swelling ratio for the PEG hydrogel group was not significantly different from the PEG hydrogels containing the MMP-sensitive peptide. Since the MMP-sensitive peptide sequence is short, the reduction in swelling ratio could be attributed to the decrease in mesh size during crosslinking. These results also suggest that CS helped in the absorption and retention of water which increased the equilibrium water content of the hydrogels. Pure CS and HA hydrogels have the greatest swelling ratio because they both have high molecular weight thus their ability to expand during water absorption is much greater than the other hydrogels incorporating PEG.

Figure 2:
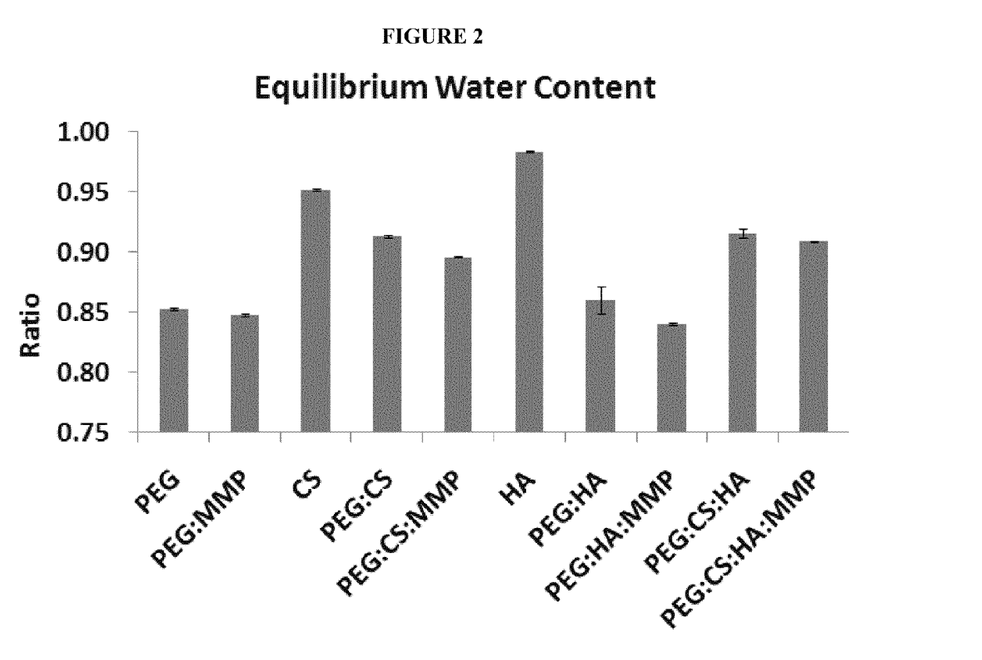
FIG. 2 is a graph depicting the equilibrium water content for each hydrogel construct.

It was further observed that the equilibrium content was similar for all hydrogels containing CS with ratios of ~0.9, whereas the hydrogel constructs without CS had lower ratios ranging from 0.76 to 0.86 (FIG. 2). The equilibrium water content of the hydrogel groups follows the same trend as their swelling ratios. The swelling ratio and equilibrium water content of the 20% w/v PEG hydrogels were comparable to the values reported earlier by Bryant et al. The significant increase in the swelling ratio and equilibrium water content when CS was added to the PEG hydrogels was consistent with the results obtained by Li et al. who also found that pure CS hydrogels swelled and absorbed more water than PEG hydrogels.

Figure 7:
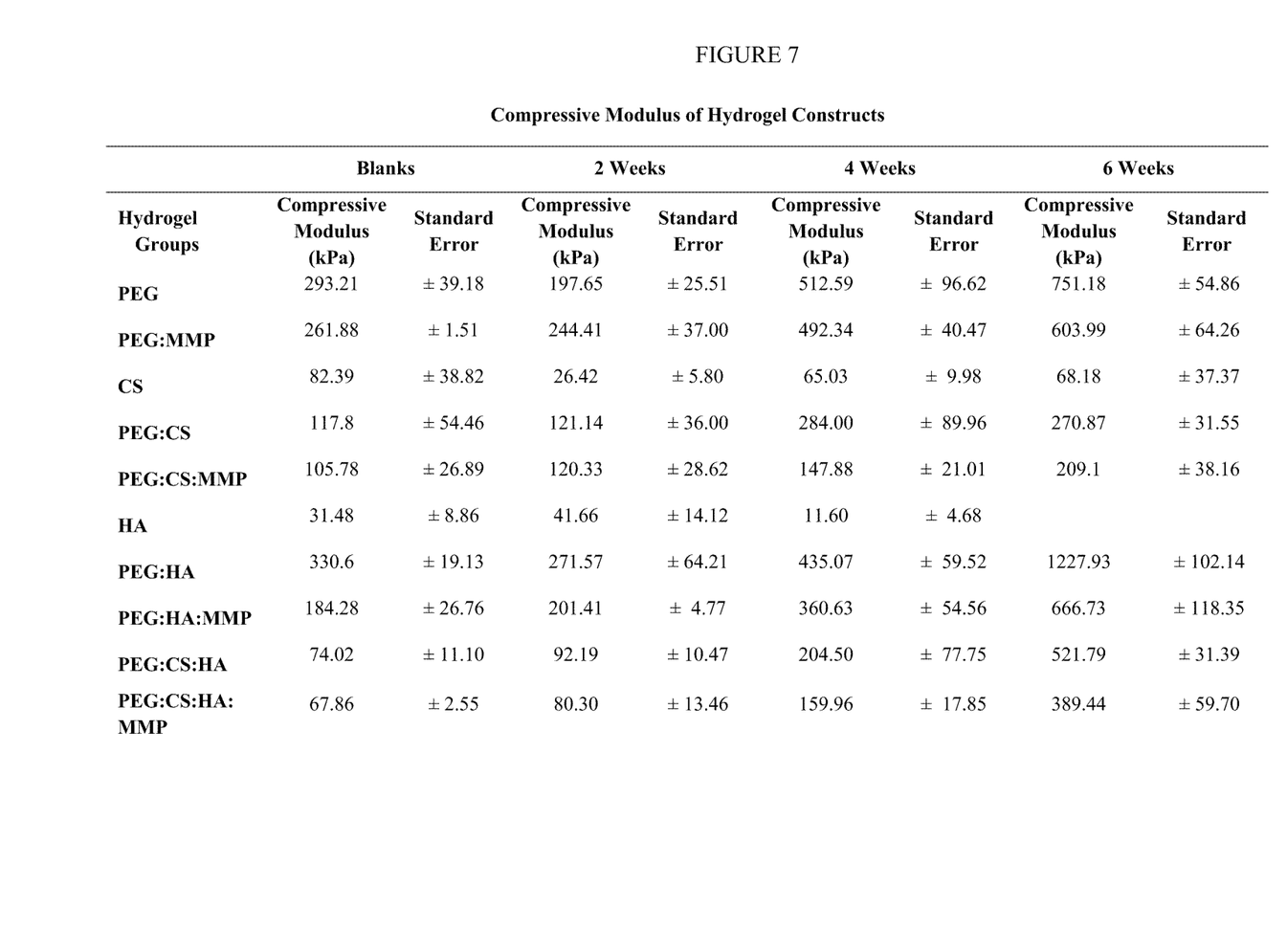
FIG. 7 is a table indicating the compressive moduli of certain multi-layer hydrogel constructs.

The compressive moduli of the various swollen hydrogels represent their ability to withstand compression and are shown in FIG. 7. The results indicate that the compressive modulus increases with time for the majority of hydrogels at the 4 and 6 week time points. The exceptions are PEG, CS and HA hydrogels. At 2 weeks the PEG and CS hydrogel groups showed a decrease in compressive modulus. The HA group showed an initial increase in compressive modulus at 2 weeks, but significantly decreased at 4 weeks and by 6 weeks the compressive modulus could not be obtained due to the complete degradation of the hydrogels.

Figure 3:
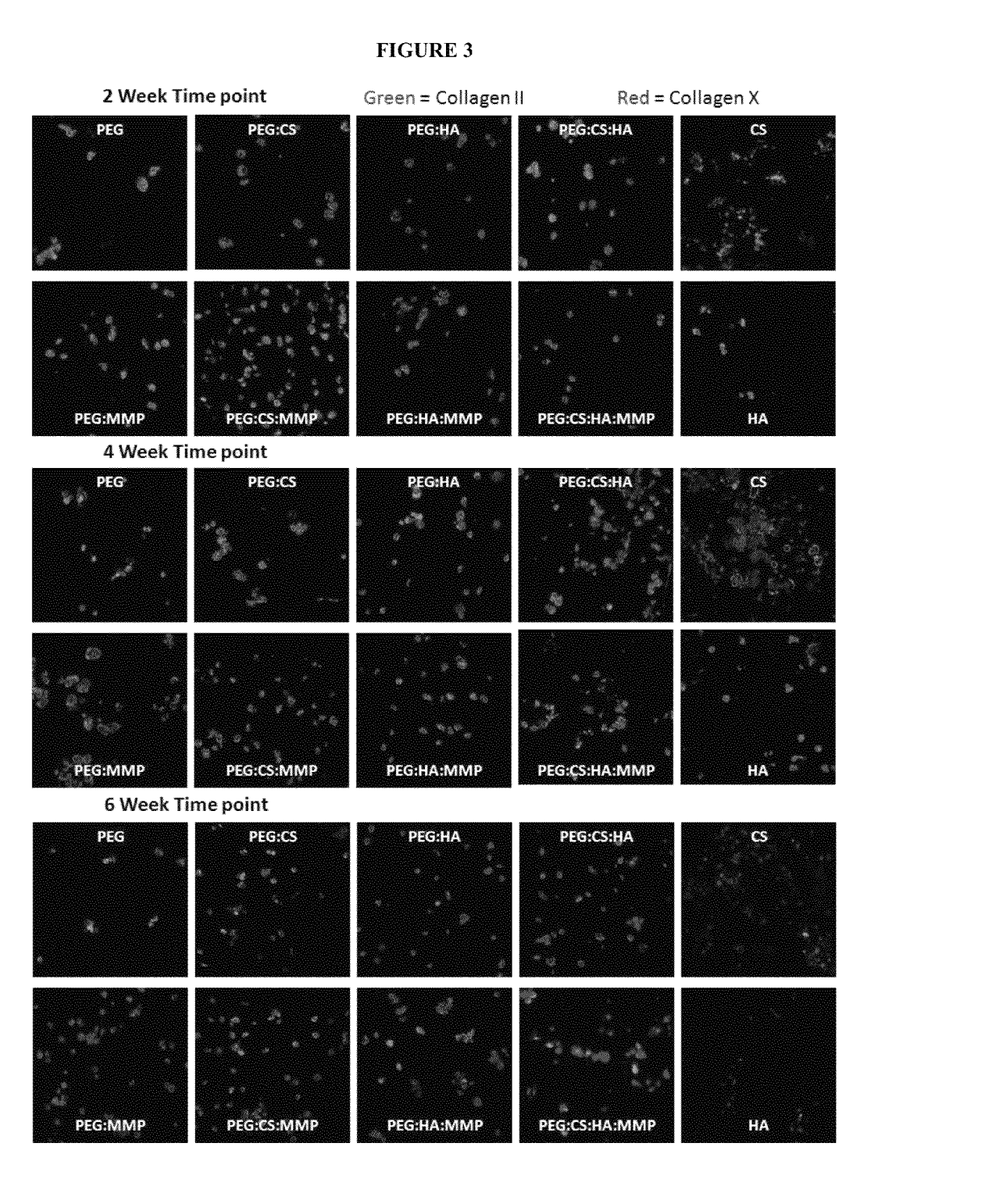
FIG. 3 depicts immunohistochemical staining images of paraffin-embedded sections of hydrogels constructs at 2, 4 and 6 weeks for collagen II (green) and X (red) taken by a fluorescence microscope at 63×. At all time points, the fluorescent images showed positive staining for both collagen II and X.

To evaluate chondrogenesis, D1 mouse progenitor cells were encapsulated within each hydrogel group and cultured for 2, 4, and 6 weeks. To verify chondrogenesis, the hydrogels were stained for type II and type X collagen. Collagen II makes up approximately 90% of the collagen in articular cartilage and collagen X is only produced by the hypertrophic chondrocytes in the calcified cartilage zone. The immunohistochemistry staining shown in FIG. 3 showed significant differences between 2 and 6 weeks. At 2 weeks the BMSCs in all hydrogel groups produced more type II collagen; however after 6 weeks of culture type, X collagen production dominated, which is in agreement with the RT-PCR data. Maximum staining for type X collagen was observed in pure CS based hydrogels for all time points, which indicated that the majority of chondrocytes in that hydrogel group were hypertrophic.

Figure 4B:
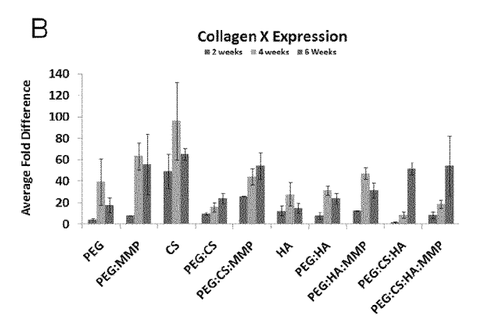
FIG. 4B is graph illustrating the average fold difference for collagen X for each hydrogel construct.
Figure 4C:
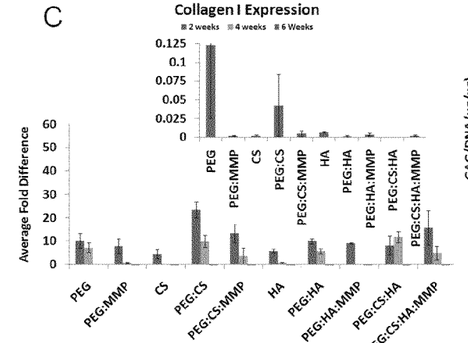
FIG. 4C is graph illustrating the average fold difference for collagen I for each hydrogel construct.

For quantitative analysis, the genetic expression of collagen II, X and I within the hydrogel constructs cultured in chondrogenic media containing TGF-$\beta$1 was also tested and compared to the gene expression of undifferentiated BMSCs that were encapsulated in PEG hydrogels cultured in DMEM. Encapsulated BMSCs were used as the comparative control to be able to compare the effects of the biomaterial composition, because using 2D plated cells as a base for comparison would not be as accurate due to the variation between 2D versus 3D environment. In addition, type I collagen was looked at to determine fibrocartilage formation. The average fold difference for collagen II, X and I for each hydrogel construct are shown in FIGS. 4A, 4B and 4C, respectively. The RT-PCR results for the gene expression of type I, II and X collagens were in accordance with previous studies demonstrating that the encapsulated BMSCs showed a temporal expression of the collagens, with early expression of type I, followed by the expression of collagen II and terminating with the increasing expression of collagen X. Undifferentiated MSCs have been shown to uniformly express type I collagen. Additionally, type I collagen is a genetic marker for fibrocartilage because it is the only type of cartilage that contains type I collagen in addition to the normal type II collagen. Therefore, type I collagen expression was used to determine BMSC differentiation and formation of fibrocartilage.

For all hydrogel groups type I collagen was present at low levels at 2 weeks and steadily decreased to a negligible level at 6 weeks. The decrease in type I collagen was an indication that the type I collagen expression was from undifferentiated cells and not from the formation of fibrocartilage. If the MSCs were differentiating into fibrocartilage then the type I collagen expression would increase with time instead of decrease. The addition of CS to the PEG hydrogels only significantly increased the collagen II expression at the 2 week time point. However, at all time points, the combined addition of CS and the MMP-sensitive peptide into the PEG hydrogels significantly increased collagen II expression indicating that the combination of CS and the MMP-sensitive peptide enhanced chondrogenesis. The addition of HA to the PEG hydrogels had no significant effect on the collagen II expression, however the combined addition of HA and the MMP-sensitive peptide to PEG hydrogels significantly increased the collagen II expression at all time points. Although, the combined addition of CS and the MMP-sensitive peptide as well as HA and the MMP-sensitive peptide to the PEG hydrogels significantly increased the collagen II expression, the PEG:CS:MMP hydrogels have significantly higher collagen II expression than the PEG:HA:MMP hydrogels, at 2 weeks. The results demonstrated that the interactions of CS and the MMP-sensitive peptide were initially more favorable than the HA and the MMP-sensitive peptide interaction for chondrogenesis.

Collagen II expression for all hydrogel compositions was relatively high at 2 weeks and continued to increase at 4 weeks for most hydrogel groups. By 6 weeks, however, type II collagen expression decreased, while type X collagen increased in all hydrogel groups. Type X collagen is only produced by hypertrophic chondrocytes, thus the increase in type X collagen indicated that chondrogenesis occurs up to 4 weeks and by 6 weeks all the chondrocytes become hypertrophic. Chondrocytes undergo terminal differentiation when they become hypertrophic and begin endochondral ossification resulting in the creation of bone tissue. The pure CS hydrogel group had the highest significantly different ($p<0.05$) collagen X expression than all other hydrogel groups for both 2 and 4 weeks. At 6 weeks the collagen X expression decreased in all groups except those that contained CS in their hydrogel composition, where collagen X expression continued to increase. This implied that CS plays a role in inducing chondrogenesis into the hypertrophic phenotype. Relatively low levels of Type I collagen gene expression were present in all hydrogel groups at 2 weeks and steadily decreased to a nonexistent level at 6 weeks. At 2 and 4 weeks, the PEG:CS hydrogel group had significantly higher collagen I expression than almost all other hydrogel groups. Both the pure CS and HA hydrogel groups had collagen I expression that was significantly lower than almost all other hydrogel groups. The down regulation of type I collagen expression at 6 weeks verified that chondrogenesis was directed towards the articular cartilage and not the fibrocartilage phenotype. Thus, according to the gene expression data, the BMSCs within all hydrogel groups began differentiation at 2 weeks and continued to differentiate into chondrocytes up to 4 weeks. At 6 weeks, although there were very few undifferentiated cells, the majority of the chondrocytes had undergone terminal differentiation into the hypertrophic phenotype.

Figure 4D:
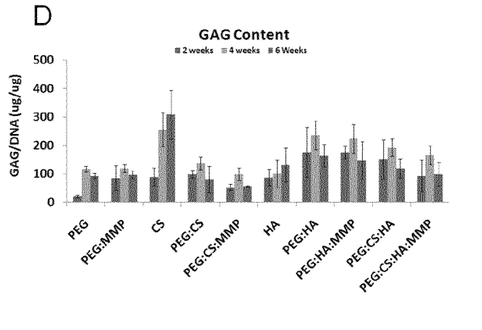
FIG. 4D is a graph illustrating the GAG concentration for each hydrogel construct.

Biochemical results for GAG production shown in FIG. 4D indicated that the matrix accumulation was dependant on biomaterial composition and time spent in culture. Given the differences in material composition and cell density of the hydrogels, matrix present in blanked hydrogels were subtracted as background and matrix accumulation was normalized to DNA content to observe differences in the biosynthetic activity of the cells within each hydrogel group. At 2 weeks, the addition of CS to the PEG hydrogels significantly increased the GAG production. Greater matrix accumulation was observed in hydrogel groups containing HA compared to those that did not, indicating that the presence of HA within the hydrogel construct enhances GAG production. The GAG concentration increased between 2 and 4 weeks for all hydrogel groups but dropped off at 6 weeks with the exception of the CS and HA groups. The cause for the continued increase in GAG production in these two hydrogel groups is unclear but it is speculated that the structural integrity of these hydrogels at 6 weeks played a role. From the degradation results, it was determined that the pure CS and HA hydrogels degraded very rapidly and this degradation was seen during the differentiation studies, where the pure CS and HA hydrogels degraded with time and by 6 weeks the hydrogels were no longer fully intact. Hydrogels without PEG lacked mechanical stability as shown by the hydrogels' compressive modulus. Mechanical strength is important for the structural support of the cells within these constructs. Without the structural support the cells are compensating by attempting to produce their own ECM, therefore increasing the GAG production even at 6 weeks within the CS and HA hydrogels. The cells within the other hydrogel groups show a decrease in GAG production because once they have reached the maximum GAG content, which usually occurs at 21 days, they stopped producing more GAG and began to break down the GAG during remodeling. These findings illustrate the capacity of BMSCs for biochemical activity within the various hydrogel compositions. Additionally, the RT-PCR and biochemical assays results indicated that specific hydrogel compositions have unique regulation of chondrogenic genes and GAG production that correlate to the specific zones of articular cartilage.

Figure 4E:
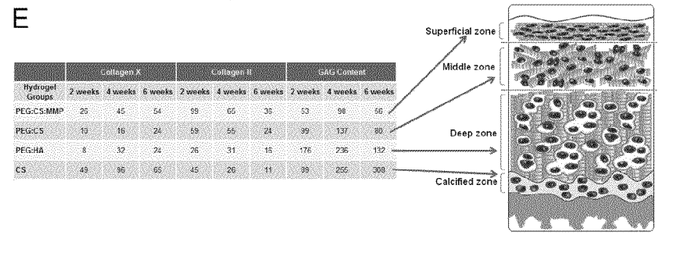
FIG. 4E is a graph depicting the correlation of cartilage generated in various hydrogel compositions to the specific zones of articular cartilage.

These observations demonstrate that biomaterial composition not only induces the BMSCs to differentiate but that the differentiation can be directed into specific zones of articular cartilage. FIG. 4E illustrates the correlation between the biomaterial composition and the specific zone of articular cartilage. The PEG:CS:MMP hydrogel composition had the highest collagen II expression as well as the lowest GAG production for 2, 4, and 6 weeks, which can be correlated to the superficial zone of articular cartilage. The PEG:CS composition had midrange expression of collagen II and GAG content for all time points which is similar to that of the middle zone. The PEG:HA hydrogel composition can be correlated to the deep zone of articular cartilage because of its high GAG content and low expression of collage II. The BMSCs within the CS hydrogel composition differentiated into hypertrophic chondrocytes with very high expression of collagen X, thus the CS hydrogel composition can be used to induce chondrogenesis specific to the calcified cartilage zone. The GAG concentration was correlated to the changes in mechanical properties of each zone. The compressive modulus of articular cartilage increased significantly with depth, ranging from the articular surface to the deep zone. The compressive modulus of the hydrogel constructs correlated to each zone of articular cartilage with PEG:CS:MMP having the lowest compressive modulus, followed by PEG:CS, and PEG:HA having the highest compressive modulus. Based on these results, these compositions were to mimic the zones of articular cartilage to create a single multi-layer hydrogel construct that would induce the simultaneous differentiation of the BMSCs into all four zones of articular cartilage to form a structural and fully functional tissue.

Figure 5A:
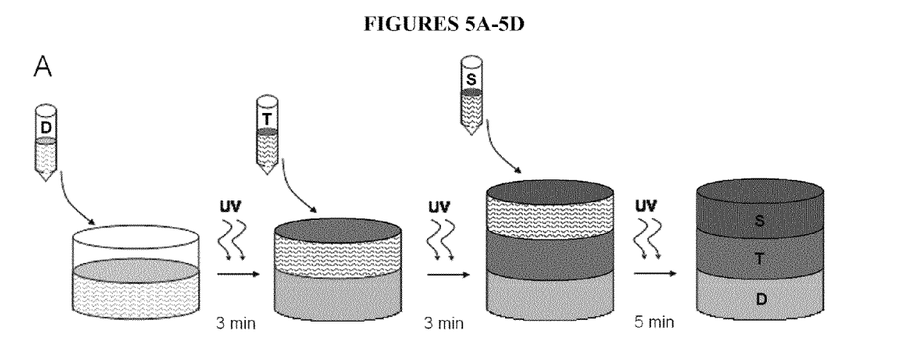
FIG. 5A is a schematic illustration of a method of fabricating a multi-layered hydrogel construct of the present disclosure, according to one embodiment.
Figure 5B:
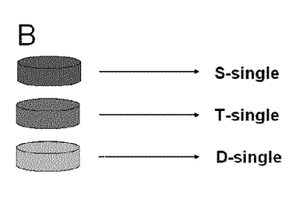
FIG. 5B is a schematic illustration of each layer of a multi-layered hydrogel construct of the present disclosure, according to one embodiment.
Figure 5C:
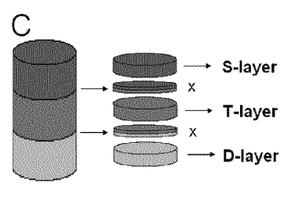
FIG. 5C is a schematic illustration depicting the separation of each layer of a multi-layered hydrogel construct of the present disclosure so that each layer may be analyzed individually.
Figure 5D:
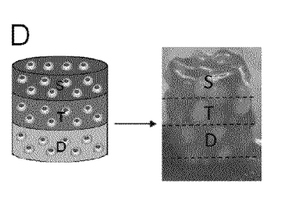
FIG. 5D is a schematic illustration depicting that after two weeks of culture, a multi-layered hydrogel construct of the present disclosure shows distinct formations of chondrons, which are chydrocytes that are surrounded by the pericellular and territorial proteoglycans.

To evaluate the feasibility of inducing zone specific chondrogenesis, a multi-layer hydrogel consisting of three layers with PEG:CS:MMP for the superficial layer, PEG:CS for the transitional layer, and PEG:HA for the deep layer was constructed. The CS layer was excluded in the initial study because the properties of this layer are less understood. D1 mouse progenitor cells were encapsulated within each layer and cultured for 2 and 4 weeks. Single layer hydrogels were also created with the same material composition as controls and to demonstrate repeatability. FIG. 5A illustrates a multi-layer fabrication method according to one embodiment. FIGS. 5B and 5C show a schematic of how the single and multi-layer hydrogels were analyzed. As demonstrated in the illustration, the interfaces of the multi-layer structure were excluded from the evaluation of gene expression. FIG. 5D illustrates a multi-layer hydrogel that has been cultured for 2 weeks, showing visible chondron formation similar to that of native cartilage.

Figure 6A:
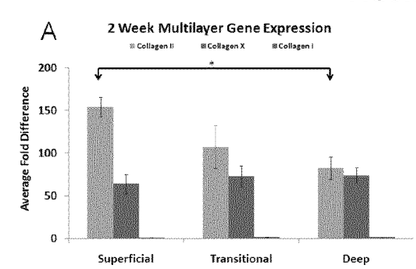
FIG. 6A is a graph illustrating the average fold difference for gene expression of collagen II, X and I at two weeks within each layer of the multi-layer hydrogel construct.
Figure 6B:
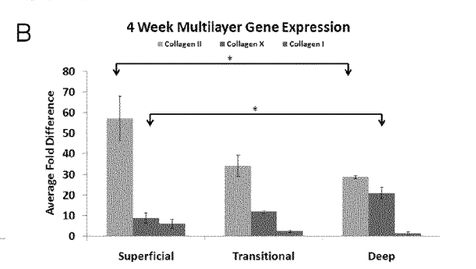
FIG. 6B is a graph illustrating the average fold difference for gene expression of collagen II, X and I at four weeks within each layer of the multi-layer hydrogel construct.

To verify chondrogenesis, the genetic expression of collagen II, collagen X and collagen I was tested. The average fold difference for collagen II, X and I for the 2 and 4 week multi-layered hydrogels are shown in FIGS. 6A and 6B, respectively. At 2 weeks, the superficial layer of the multi-layer hydrogel exhibited significantly ($p<0.05$) higher collagen II expression than the deep layer. However, the genetic expression for collagen X of the multi-layer hydrogel at 2 weeks, showed no difference between the layers. There is still a small basal level expression of type I collagen in multi-layer hydrogels at 2 weeks. At 4 weeks, the superficial layer had significantly higher collagen II expression then the deep layer. Within the deep layer however, the collagen X expression was significantly higher than that of the superficial layer.

Figure 6C:
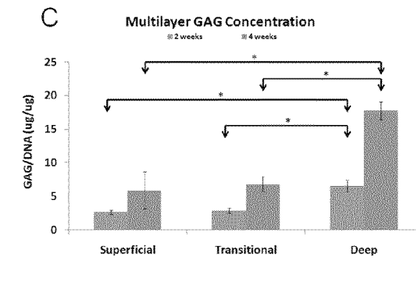
FIG. 6C is a graph illustrating the GAG concentration at two and four weeks within each layer of the multi-layer hydrogel construct.
Figure 6D:
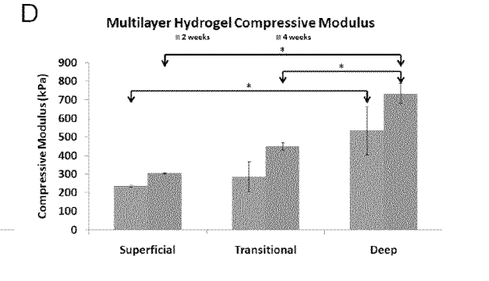
FIG. 6D is a graph illustrating the compressive modulus at two and four weeks of each layer of the multi-layer hydrogel construct.

Additionally, to verify functionality, the GAG production within the multi-layer constructs at 2 and 4 weeks was determined. As shown in FIG. 6C, the GAG production increased with time. Furthermore, the cells within the deep layer exhibited significantly higher GAG production than in the superficial layer at both 2 and 4 weeks. Articular cartilage's main function is to resist compression, thus it was desirable that a multi-layer construct of the present disclosure have similar compressive strength to that of native cartilage. The compression data shown in FIG. 6D indicated that the compressive modulus increased from the superficial to the transitional and then to the deep layer, with significant difference (p<0.05) between the superficial and the deep layer at both 2 and 4 weeks. These results are in compliance with the mechanical properties of the native cartilage, which have the highest compressive strength in the deep layer due to the increase in GAG content.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

1. Burdick, J. A. and K. S. Anseth, *Photoencapsulation of osteoblasts in injectable RGD-modified PEG hydrogels for bone tissue engineering*. Biomaterials, 2002. 23(22): p. 4315-23.
2. Bryant, S. J., et al., *Encapsulating chondrocytes in degrading PEG hydrogels with high modulus: engineering gel structural changes to facilitate cartilaginous tissue production*. Biotechnol Bioeng, 2004. 86(7): p. 747-55.
3. Bryant, S. J., et al., *Crosslinking density influences the morphology of chondrocytes photoencapsulated in PEG hydrogels during the application of compressive strain*. J Orthop Res, 2004. 22(5): p. 1143-9.
4. Bryant, S. J. and K. S. Anseth, *Controlling the spatial distribution of ECM components in degradable PEG hydrogels for tissue engineering cartilage*. J Biomed Mater Res A, 2003. 64(1): p. 70-9.
5. Alcantar, N. A., E. S. Aydil, and J. N. Israelachvili, *Polyethylene glycol-coated biocompatible surfaces*. J Biomed Mater Res, 2000. 51(3): p. 343-51.
6. Klein, T. J., et al., *Tissue Engineering of Articular Cartilage with Biomimetic Zones*. Tissue Eng Part B Rev, 2009.
7. Sharma, B., et al., *Designing zonal organization into tissue-engineered cartilage*. Tissue Eng, 2007. 13(2): p. 405-14.
8. Ng, K. W., G. A. Ateshian, and C. T. Hung, *Zonal chondrocytes seeded in a layered agarose hydrogel create engineered cartilage with depth-dependent cellular and mechanical inhomogeneity*. Tissue Eng Part A, 2009. 15(9): p. 2315-24.
9. Schinagl, R. M., et al., *Depth-dependent confined compression modulus of full-thickness bovine articular cartilage*. J Orthop Res, 1997. 15(4): p. 499-506.
10. Bhosale, A. M. and J. B. Richardson, *Articular cartilage: structure, injuries and review of management*. Br Med Bull, 2008. 87: p. 77-95.
11. Poole, A. R., et al., *Composition and structure of articular cartilage: a template for tissue repair*. Clin Orthop Relat Res, 2001 (391 Suppl): p. S26-33.
12. Einhorn, T. A., R. J. O'Keefe, and J. A. Buckwalter, *Orthopaedic Basic Science Foundations of Clinical Practice*. 3 ed. 2007: American Academy of Orthopaedic Surgeons.
13. Chen, G., Ushida, Takashi, Tateishi, Tetsuya, *Scaffold Design for Tissue Engineering*. Macromolecular Bioscience, 2002. 2: p. 67-77.
14. Varghese, S., et al., *Chondroitin sulfate based niches for chondrogenic differentiation of mesenchymal stem cells*. Matrix Biol, 2008. 27(1): p. 12-21.
15. Butnariu-Ephrat, M., et al., *Resurfacing of goat articular cartilage by chondrocytes derived from bone marrow*. Clin Orthop Relat Res, 1996 (330): p. 234-43.
16. Nuttelman, C. R., M. C. Tripodi, and K. S. Anseth, *In vitro osteogenic differentiation of human mesenchymal stem cells photoencapsulated in PEG hydrogels*. J Biomed Mater Res A, 2004. 68(4): p. 773-82.
17. Kim, S., et al., *Synthetic MMP-13 degradable ECMs based on poly(N-isopropylacrylamide-co-acrylic acid) semi-interpenetrating polymer networks. I. Degradation and cell migration*. J Biomed Mater Res A, 2005. 75(1): p. 73-88.
18. Kim, S. and K. E. Healy, *Synthesis and characterization of injectable poly(N-isopropylacrylamide-co-acrylic acid) hydrogels with proteolytically degradable cross-links*. Biomacromolecules, 2003. 4(5): p. 1214-23.
19. Seliktar, D., et al., *MMP-2 sensitive, VEGF-bearing bioactive hydrogels for promotion of vascular healing*. J Biomed Mater Res A, 2004. 68(4): p. 704-16.
20. Bryant, S. J. and K. S. Anseth, *Hydrogel properties influence ECM production by chondrocytes photoencapsulated in poly(ethylene glycol) hydrogels*. J Biomed Mater Res, 2002. 59(1): p. 63-72.
21. Barry, F., et al., *Chondrogenic differentiation of mesenchymal stem cells from bone marrow: differentiation-dependent gene expression of matrix components*. Exp Cell Res, 2001. 268(2): p. 189-200.
22. Williams, C. G., et al., *In vitro chondrogenesis of bone marrow-derived mesenchymal stem cells in a photopolymerizing hydrogel*. Tissue Eng, 2003. 9(4): p. 679-88.
23. Eyre, D. R. and J. J. Wu, *Collagen of fibrocartilage: a distinctive molecular phenotype in bovine meniscus*. FEBS Lett, 1983. 158(2): p. 265-70.
24. Harper, J. and M. Klagsbrun, *Cartilage to bone—angiogenesis leads the way*. Nat Med, 1999. 5(6): p. 617-8.
25. He, X. and E. Jabbari, Material properties and cytocompatibility of injectable MMP degradable poly(lactide ethylene oxide fumarate) hydrogel as a carrier for marrow stromal cells. Biomacromolecules, 2007. 8(3): p. 780-92.

26. Leach, B. J., Bivens, K. A. Patrick, C. W., Jr., Schmidt, C. E., Photocrosslinked hyaluronic acid hydrogels: natural, biodegradable tissue engineering scaffolds. Biotechnol Bioeng, 2003. 82(5): p. 578-89.

What is claimed is:

1. A multi-layered hydrogel construct comprising:
 a first layer comprising a first polymerizable material, hyaluronic acid and a plurality of cells;
 a second layer comprising a second polymerizable material, chondroitin sulfate and a plurality of cells; and
 a third layer comprising a third polymerizable material, chondroitin sulfate, a matrix metalloprotease sensitive peptide, and a plurality of cells.

2. The hydrogel construct of claim 1 wherein the plurality of cells comprise mesenchymal stem cells, progenitor cells, bone marrow stromal cells, or adipose-derived stem cells.

3. The hydrogel construct of claim 1 wherein the first polymerizable material, the second polymerizable material, or the third polymerizable material comprises photopolymerizable poly(ethylene glycol) diacrylate (PEGDA) or dimethacrylate (PEGDMA) or multifunctional poly(ethylene glycol) vinylsulfones (PEGVS) or sulfhydryls (PEGSH).

4. The hydrogel construct of claim 1 wherein the hyaluronic acid is present in the first layer in an amount of about 0.5 to about 3% (w/v).

5. The hydrogel construct of claim 1 wherein the chondroitin sulfate is present in the second layer in an amount of about 5% to about 20% (w/v).

6. The hydrogel construct of claim 1 wherein the chondroitin sulfate is present in the third layer in an amount of about 5% to about 20% (w/v) and the MMP-sensitive peptide is present in the third layer in an amount of about 1 to about 10% (w/v).

7. The hydrogel construct of claim 1 wherein the first polymerizable material, the second polymerizable material, and the third polymerizable material are the same material.

8. The hydrogel construct of claim 1 wherein the first polymerizable material, the second polymerizable material, and the third polymerizable material comprise photopolymerizable poly(ethylene glycol) diacrylate (PEGDA) or dimethacrylate (PEGDMA) or multifunctional poly(ethylene glycol) vinylsulfones (PEGVS) or sulfhydryls (PEGSH).

9. The hydrogel construct of claim 1 further comprising a fourth layer.

* * * * *